(12) United States Patent
Lee et al.

(10) Patent No.: US 6,248,265 B1
(45) Date of Patent: Jun. 19, 2001

(54) CLEAN GENERATION OF A FLUOROARYL GRIGNARD REAGENT

(75) Inventors: John Y. Lee; David W. Owens; Charles R. Everly; Ronny W. Lin; John M. Power; Steven P. Diefenbach, all of Baton Rouge, LA (US); Niomi L. Krzystowczyk, Orangeburg, SC (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/596,146

(22) Filed: Jun. 16, 2000

Related U.S. Application Data

(63) Continuation-in-part of application No. 09/216,463, filed on Dec. 18, 1998, now Pat. No. 6,129,863.

(51) Int. Cl.[7] .............................. C07F 3/02; C07B 49/00
(52) U.S. Cl. .................................. 260/665; 568/1; 568/6; 532/1; 260/1
(58) Field of Search .............................. 260/665, 665 G, 260/7; 568/1, 6; 532/1

(56) References Cited

U.S. PATENT DOCUMENTS

| | | | |
|---|---|---|---|
| 5,189,222 | 2/1993 | Ashby et al. | 568/1 |
| 5,362,423 | 11/1994 | Ikeda et al. | 260/665 R |
| 5,399,780 | 3/1995 | Ikeda et al. | 568/1 |
| 5,468,819 | 11/1995 | Goodall et al. | 526/171 |
| 5,473,036 | 12/1995 | Piotrowski et al. | 528/4 |
| 5,600,004 | 2/1997 | Diefenbach | 568/1 |
| 5,621,126 | 4/1997 | Canich et al. | 556/9 |
| 5,693,261 | 12/1997 | Krzystowczyk et al. | 260/665 G |

FOREIGN PATENT DOCUMENTS

| | | |
|---|---|---|
| 0604963 | 7/1994 | (EP) . |
| 0604963 A1 * | 7/1994 | (EP) ................... C07F/5/02 |
| 0728760 | 8/1996 | (EP) . |
| 705719 | 3/1954 | (GB) . |

OTHER PUBLICATIONS

Fujiki et al, Syntheses and lipophilicities of tetraarylborate ions substituted with many trifluoromethyl groups, Journal of Fluorine Chemistry, vol. 57 pp. 307–321, 1992.*

Nield, E. et al., "Aromatic Polyfluoro–compounds. Part I. The Synthesis of Aromatic Polyfluoro–compounds from Pentafluorobenzene", J. Chem. Soc., 1959, pp. 166–171.

Respess, W. L. et al., "A New Synthesis of Perfluoroaromatic Grignard Reagents", J. Organometal. Chem., vol. 18, 1969, pp. 263–274.

Respess, William L. et al., "Synthesis of Some Pentafluorophenylmagnesium Compounds", J. Organometal. Chem., vol. 11, 1968, pp. 619–622.

Harper, Jr. Robert J. et al., "Reactions of Organometallics with Fluoroaromatic Compounds[1]", J. Organic Chem., vol. 29, 1964, pp. 2385–2389.

Respess, W. L. et al., "The Preparation of a Grignard Reagent From Hexafluorobenzene by the Entrainment Technique", J. Organometal. Chem., vol. 19, 1969, pp. 191–195.

Kobayashi, Hiroshi et al., "Synthesis of Trifluoromethylated Tetraphenylborates and Solvent–extraction Properties of their Ion–associates with Alkali–metal Ions", Rep. Asahi Glass Found. Ind. Technol, vol. 42, 1983, pp. 137–145 (not translated).

Zakharkin, L. I. et al., "Effect of Solvents on Reactions of Organometallic Compounds; II. Exchange of Radicals Between $Rm_gX$ And R'X", J. Organometal. Chem., vol. 2, 1964, pp. 309–313.

Brookhart et al., "$[(3,5-(CF_3)_2C_6H_4B]^-[H(OEt_2)_2]^+$ A Convenient Reagent For Generation and Stabilization of Cationic, Highly Electrophilic Organometallic Complexes", Organometallics, 1992, vol. 11, pp. 3920–3922.

Fujiki et al., "Synthesis and Lipophilicites of Tetraarylborate ions Substituted with many Trifluoromethyl Groups", Journal of Fluorine Chemistry, 1992, vol. 57, pp. 307–321.

Nishida et al., "Tetrakis[3,5–bis(trifluoromethyl)phenyl]borate. Highly Lipophilic Stable Anionic Agent for Solvent–extraction of Cations", Bull Chem. Soc. Jpn., 1984, vol. 57, No. 9, pp. 2600–2604.

* cited by examiner

Primary Examiner—Johann Richter
Assistant Examiner—Diedra Faulkner
(74) Attorney, Agent, or Firm—Philip M. Pippenger

(57) ABSTRACT

Fluoroaryl Grignard reagents are produced from a hydrocarbyl Grignard reagent and fluoroaromatic compounds via separate additions of different fluoroaromatic compounds, such that the conversion of hydrocarbyl Grignard reagent to the desired fluoroaryl Grignard reagent is essentially complete, and thus the reaction product is free or essentially free of agents that may negatively affect subsequent reactions. The fluoroaryl Grignard reagents may be further reacted with boron trihalides in order to obtain tris (fluoroaryl)boranes or tetrakis(fluoroaryl)borates.

30 Claims, No Drawings

CLEAN GENERATION OF A FLUOROARYL GRIGNARD REAGENT

REFERENCE TO RELATED APPLICATIONS

This application is a continuation-in-part of commonly-owned U.S. application Ser. No. 09/216,463, filed Dec. 18, 1998, now U.S. Pat. No. 6,129,863, issued Oct. 10, 2000.

TECHNICAL FIELD

This invention concerns a process in which fluoroaromatic compounds are converted to fluoroaryl Grignard reagents via reaction with hydrocarbyl Grignard reagents, and further processes that utilize these fluoroaryl Grignard reagents.

BACKGROUND

Perfluoroaryl Grignard reagents are useful in the synthesis of metal and metalloid perfluoroaryl compounds. Many preparations of perfluoroaryl Grignard reagents are known in the literature, some of which call for stoichiometric amounts of Grignard reagent and the polyhaloaromatic compound, J. Organomet. Chem., 1969, 18, 263–274, and J. Organomet. Chem., 1968,11,619–622. Others describe the use of excess Grignard reagent, *J. Org. Chem.,* 1964, 29, 2385–2389, and *J. Organomet. Chem.,* 1969, 19, 191–195. While it will not be considered further here, it should be noted that perfluoroaryl Grignard reagents have been generated in which the perfluoroaryl Grignard reagent is made directly from Mg metal and the polyhaloaromatic compound, as reported in *J. Chem. Soc.,* 1959, 166–171, and *J. Org. Chem.,* 1964,29,2385–2389. Two U.S. patents describe methods for obtaining perfluoroaryl Grignard reagents, one with the Grignard reagent in excess, U.S. Pat. No. 5,362,423, and the other with the polyhaloaromatic compound in excess, U.S. Pat. No. 5,600,004.

Other fluoroaryl Grignard reagents are also useful in the synthesis of borane compounds, such as the tetraphenylborate anion, tetrakis(o-tolyl)borate anion, tetrakis(m,n-dimethylphenyl)borate anion, and tetrakis [p-(trifluoromethyl)phenyl]borate anion, which are used as cocatalysts in combination with metallocenes for olefin polymerization. See in this regard, U.S. Pat. No. 5,468,819 to Goodall et al.; U.S. Pat. No. 5,621,126 to Canich et al.; and Brookhart et al., *Organometallics,* 1992, 11, 3920.

Separation of unreacted alkyl Grignard reagent and fluoroaromatic compound starting materials from the reaction mixture is often desired, due to their interference in subsequent syntheses, but such separation is not always feasible.

THE INVENTION

This invention makes possible the formation of a fluoroaryl Grignard reagent from a hydrocarbyl Grignard reagent and fluoroaromatic compounds via separate additions of different fluoroaromatic compounds, such that the conversion of hydrocarbyl Grignard reagent to the desired fluoroaryl Grignard reagent is essentially complete, and thus the reaction product is free or essentially free of agents that may negatively affect subsequent reactions.

A first embodiment of this invention entails in step a) forming a mixture comprising (i) hydrocarbyl Grignard reagent, (ii) at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, and (iii) an anhydrous liquid organic reaction medium. The molar ratio of (i) to (ii) is greater than one, such that a reaction product mixture is formed comprising fluoroaryl Grignard reagent and excess hydrocarbyl Grignard reagent. In step b) at least a portion of the reaction product mixture produced in a) is mixed with an amount of at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, at least sufficient to react with the excess hydrocarbyl Grignard reagent, which thereby produces a further reaction product mixture composed predominately of fluoroaryl Grignard reagent and anhydrous liquid organic reaction medium.

Another embodiment of the invention involves a process which comprises a) reacting, in a liquid organic reaction medium, at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, with a stoichiometric excess of a hydrocarbyl Grignard reagent to produce a reaction product mixture comprising fluoroaryl Grignard reagent and unreacted hydrocarbyl Grignard reagent. In step b), at least a portion of the reaction product mixture produced in a) is contacted with a fluoroaromatic compound to convert at least a portion of said unreacted hydrocarbyl Grignard reagent into fluoroaryl Grignard reagent.

Still another embodiment of this invention entails a process which comprises a step b) in which a mixture comprising a fluoroaryl Grignard reagent, a hydrocarbyl Grignard reagent, and a liquid organic medium is contacted with at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, in an amount at least equivalent to the amount of said hydrocarbyl Grignard reagent. The resultant mixture is maintained at a temperature at least high enough to cause hydrocarbyl Grignard reagent to be converted into fluoroaryl Grignard reagent.

In another embodiment of this invention, a) a mixture is formed comprising (i) hydrocarbyl Grignard reagent, (ii) at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, and (iii) an anhydrous liquid organic reaction medium. In this mixture, the molar ratio of (i) to (ii) is greater than one, such that a reaction product mixture is formed comprising fluoroaryl Grignard reagent and excess hydrocarbyl Grignard reagent. In step b), at least a portion of the reaction product mixture produced in a) is mixed with an amount of at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, such amount being in excess relative to the excess hydrocarbyl Grignard reagent such that a further reaction product mixture is produced composed predominately of fluoroaryl Grignard reagent, anhdydrous liquid organic reaction medium, and unreacted fluoroaromatic compound. In step c), a boron trihalide, a boron trihalide-solvent complex, or an alkyl borate is mixed with at least a portion of the reaction product mixture produced in b) in proportions such that a tris(fluoroaryl)borane is produced.

A further embodiment of this invention involves a) forming a mixture comprising (i) hydrocarbyl Grignard reagent, (ii) at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, and (iii) an anhydrous liquid organic reaction medium. The molar ratio of (i) to (ii) added to the mixture is greater than one, such that a reaction product mixture is formed comprising fluoroaryl Grignard reagent and excess hydrocarbyl Grignard reagent. In step b), at least a portion of the reaction product mixture produced in a) is mixed with an amount of at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, such amount being in excess relative to the hydrocarbyl Grignard reagent such that there is produced a further reaction product mixture composed predominately of fluoroaryl Grignard reagent, anhydrous liquid organic reaction medium, and unreacted fluoroaromatic compound. In step c), a boron trihalide, a boron trihalide-solvent complex, or an alkyl borate is mixed with at least a portion of the reaction product mixture produced in step b) in proportions such that a salt of a tetrakis(fluoroaryl)borate anion is produced.

Further embodiments of the invention will be apparent from the ensuing description and appended claims.

The hydrocarbyl Grignard reagent is made by combining a hydrocarbyl halide and Mg in a suitable reaction medium, either the medium used for the process, or a separate medium, which is then added to the liquid organic reaction medium of the process. Alternatively, commercially available hydrocarbyl Grignard reagents may be used. The word hydrocarbyl is defined as any monovalent group derived from a linear, branched, or cyclic $C_1$ to $C_{20}$ hydrocarbon. Examples of hydrocarbyl Grignard reagents include ethylmagnesium chloride, sec-butylmagnesium bromide, cyclopentenylmagnesium chloride, cyclohexylmagnesium bromide, 3-hexenylmagnesium iodide, 4-methylcyclooctylmagnesium iodide, 6-ethyldodecylmagnesium bromide, and eicosylmagnesium chloride. Short-chain alkyl Grignard reagents, e.g., $C_1$ to $C_6$, are preferred hydrocarbyl Grignard reagents, and the preferred halogen atom of the hydrocarbyl Grignard reagent is a bromine atom. Isopropylmagnesium bromide is the most highly preferred hydrocarbyl Grignard reagent.

Throughout this document, the term "fluoroaromatic compound" shall be understood to mean, as described above, an aromatic compound in which at least two fluorine atoms, or at least two perfluorohydrocarbyl groups, or at least one fluorine atom and at least one perfluorohydrocarbyl group are bonded directly to the aromatic ring, and at least two hydrogen atoms, or at least one hydrogen atom and a halogen atom other than a fluorine atom are also bonded directly to the aromatic ring. It is preferred that at least two fluorine atoms or at least two perfluorohydrocarbyl groups are bonded directly to an aromatic ring; it is also preferred that at least one hydrogen atom and one halogen atom other than a fluorine atom are also bonded directly to the aromatic ring. The aromatic ring of the fluoroaromatic compound may be, but is not limited to, benzene, naphthalene, anthracene, biphenyl, phenanthrene, or indene. Benzene is the preferred aromatic moiety. Each position on the aromatic ring(s) of the fluoroaromatic compound that is not a fluorine atom or a perfluorohydrocarbyl group, hydrogen atom, or halogen atom other than a fluorine atom, is substituted by a hydrocarbyl group, an alkoxy group, or a silyl group. The perfluorohydrocarbyl groups include alkyl and aryl perfluorocarbons; suitable perfluorohydrocarbyl groups are, for example, trifluoromethyl, pentafluoroethyl, pentafluorophenyl, and heptafluoronaphthyl. The hydrocarbyl groups of the fluoroaromatic compounds are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. The alkoxy groups preferably have $C_1$ to $C_6$ alkyl moieties. Some examples of alkoxy groups are methoxy, ethoxy, isopropoxy, methylcyclopentoxy, and cyclohexoxy. The silyl groups preferably have $C_1$ to $C_{18}$ alkyl groups or $C_6$ to $C_{20}$ aryl or aralkyl groups. Suitable silyl groups include trimethylsilyl, triisopropylsilyl, tert-butyl(dimethyl) silyl, tridecylsilyl, and triphenylsilyl. Examples of fluoroaromatic compounds that can be used in the practice of this invention include 1-chloro-2,6-difluoro-4-[tri(isopropyl) silyl]benzene, 1-bromo-2,4-difluoro-3-[dimethyl(tert-butyl) silyl]benzene, 4-chloro-3,5-difluoro-4'-(methoxy)-biphenyl, 1-bromo-2-(isopropoxy)-3-fluoro-4-(trifluoromethyl) naphthalene, 1-bromo-3,4-bis(heptafluoropropyl)-anthracene, 2-chloro-9,10-bis(p-tolyl)-1,3-difluorophenanthrene, and 4-bromo-6,7-difluoroindene. It is preferred that at most two substituents on the ring of the fluoroaromatic compound are hydrocarbyl groups, alkoxy groups, or silyl groups. When a halogen atom other than fluorine is present on the aromatic ring, it is preferably a chlorine atom or a bromine atom.

It is highly preferred to use fluoroaromatic compounds in which the substituents consist of fluorine atoms and/or perfluorohydrocarbyl groups, hydrogen atoms, and the two atoms which are one hydrogen atom and one halogen atom other than fluorine or two hydrogen atoms. Examples of such compounds are tetrafluorobenzene, 1-chloro-2,3,5,6-tetrafluorobenzene, 1-bromo-2,3,4,6-tetrafluorobenzene, 1-iodo-2,3,4,5-tetrafluorobenzene, 1-bromo-3,5-bis (trifluoromethyl)benzene, 1-chloro-2,6-bis(trifluoromethyl) benzene, 1-chloro-2,4,6-tris(trifluoromethyl)-benzene, 4-chloro-2,3,5,2',3',4',5',6'-octafluorobiphenyl, 2-bromo-3,5, 2',3',4', 5',6'-heptafluoro-4-(pentafluoroethyl)biphenyl, 3,4, 5,2',3',5 '-hexa-fluoro-2,6-bis(trifluoromethyl)biphenyl, 1-chloro-3,4,5,6,7,8-hexafluoronaphthalene, 2-bromo-1,4,5, 7,8-pentafluoro-6-(trifluoromethyl)naphthalene, 2-chloro-1, 3,5,6,7,8-hexa-fluoroanthracene, 1-bromo-5,6,7,8,9,10-hexafluoro-3,4-bis(heptafluoropropyl)anthracene, 1,2,3,4,5, 6,9,10-octafluorophenanthrene, 1-bromo-2,4,5,6,7,8,9,10-octafluoro-phenanthrene, and analogous compounds.

The fluoroaromatic compound or compounds added in both steps a) and b) of the process contain a site reactive toward a hydrocarbyl Grignard reagent; this site of the fluoroaromatic compound is an iodine, bromine, chlorine, or hydrogen atom. Preferably, the fluoroaromatic compound added in a) has a chlorine atom as its Grignard-reactive site, while the fluoroaromatic compound added in b) has either a bromine atom or a hydrogen atom as its Grignard-reactive site.

In both steps a) and b), a single fluoroaromatic compound may be added, or a mixture of two or more such compounds may be used. When a mixture of different fluoroaryl Grignard reagents is desired, a mixture of fluoroaromatic compounds with different aromatic rings is added. For example, a mixture of 1-chloro-2,3,4,6-tetrafluorobenzene and 4-chloro-2,3,5,2',3',4',5',6'-octafluorobiphenyl may be added in step a), followed by the addition of 1-bromo-2,3,4,6-tetrafluorobenzene and 3,4,5,2',3',5'-hexafluoro-2,6-bis (trifluoromethyl)biphenyl. The addition of two compounds, alike save the Grignard-reactive substituent, will yield one fluoroaryl Grignard reagent. This is the preferred embodiment of the invention, and it is preferred that the mixture of fluoroaromatic compounds is added in step b) rather than in step a). It is highly preferred to add a fluoroaromatic compound which has a chlorine atom as its Grignard-reactive substituent in step a). In step b), the addition of a mixture of compounds, which have either a hydrogen atom or a bromine atom as their Grignard-reactive substituents, but are otherwise the same as the fluoroaromatic compound added in step a) or the addition of a compound which has a bromine atom as its Grignard-reactive substituent, but is otherwise the same as the fluoroaromatic compound added in step a) is highly preferred. Most highly preferred in step b) is the addition of a fluoroaromatic compound that is the same as that added in step a) except that the Grignard-reactive substituent is a bromine atom.

Preferably, the liquid organic reaction medium is an ether-containing medium. This medium may be comprised of one or more ethers, and may, at various points, also contain one or more other types of components, such as hydrocarbons or hydrocarbyl halides. Any of a variety of monoethers or polyethers may be used, including diisopropyl ether, dibutyl ether, tetrahydrofuran, 1,4-dioxane, cyclohexyl methyl ether, diglyme, triglyme, and tetraglyme. Diethyl ether is a preferred liquid organic reaction medium in the practice of this invention.

The amount of hydrocarbyl Grignard reagent added in step a) of the process should be in molar excess of the amount of fluoroaromatic compound added in step a) of the process. The preferred molar excess is in the range of from about 1.01 mole hydrocarbyl Grignard reagent per mole fluoroaromatic compound to about 1.25 mole hydrocarbyl Grignard reagent per mole fluoroaromatic compound. Most desirable is a molar excess of about 1.05 to about 1.15 mole hydrocarbyl Grignard reagent per mole fluoroaromatic compound.

In step b) of the process of this invention, the amount of fluoroaromatic compound(s) is in at least sufficient excess relative to the excess hydrocarbyl Grignard reagent present such that the reaction product mixture comprises excess, unreacted fluoroaromatic compound. Sufficient excess of fluoroaromatic compound in b) is a molar amount larger than the excess molar amount of hydrocarbyl Grignard reagent added in a). It is necessary to add more than the stoichiometric amount of fluoroaromatic compound to react with the expected excess hydrocarbyl Grignard reagent in order to drive the reaction, much as the excess hydrocarbyl Grignard reagent drives the reaction in a). The molar amount of fluoroaromatic compound typically ranges from about 1.01 to about 4 moles per excess mole of hydrocarbyl Grignard reagent, with the preferred ranges being from about 1.5 to about 2.5 moles per excess mole of hydrocarbyl Grignard reagent. The unreacted fluoroaromatic compound(s) in the reaction product mixture produced in step b) may be reacted with more hydrocarbyl Grignard reagent via back-titration in order to form more fluoroaryl Grignard reagent.

Steps a) and b) can be conducted at any temperatures below the thermal decomposition temperature of the reactants and desired products of the reactions, provided that (i) the reaction mixtures are in the liquid state under the temperature and pressure conditions being used, and (ii) the desired reaction takes place at a suitable rate of reaction under the temperature and pressure conditions being used. Reaction temperatures in steps a) and b) are often within the range of from about 0° C. to about 60° C., and more often the temperature is in the range of from about 25° C. to about 58° C. When the reactions are conducted at atmospheric pressure or at elevated pressures of up to about 20 psig (about 240 kPa), it is preferred to operate at temperatures in the range of from about 45° C. to about 56° C. Depending on the reactants and solvents being used, it may be necessary to operate under elevated pressures when using temperatures above about 60° C. In either step a) or b), or both, the mixture can be heated to a specific temperature throughout the entire reaction period, or the temperature may be increased or decreased one or more times during the reaction period, provided of course that the temperature does not exceed the thermal decomposition temperature of the desired product of the reaction. In both steps a) and b) of the process, it is preferred to heat the mixture after the various components have been added, although one or more preheated feeds may be employed.

While the contact time for the various components of the reaction can be anywhere from two to twenty hours, a preferred range is from about three to about fifteen hours. The contact time is more preferably from about four to about ten hours.

In a highly preferred practice of the invention, fluoroaryl Grignard reagents are produced when the hydrocarbyl Grignard reagent is isopropylmagnesium bromide; the fluoroaromatic compound in step a) has a chlorine atom as its Grignard-reactive substituent; the fluoroaromatic compound in step b) has a bromine atom as its Grignard-reactive substituent; and (iii) in a) is a liquid ethereal reaction medium. The reaction product mixture produced in b) is thus composed predominately of fluoroarylmagnesium bromide, isopropyl chloride, isopropyl bromide, fluoroaromatic compound which has a bromine atom as its Grignard-reactive substituent, and liquid ethereal reaction medium. The fluoroaromatic compound which has a bromine atom as its Grignard-reactive substituent in the reaction product mixture produced in b) is then consumed in situ by back-titration with isopropylmagnesium bromide to form more fluoroarylmagnesium bromide.

The term "boron trihalide" includes boron trifluoride, boron trichloride, boron tribromide, boron triiodide, or any mixed-halogen boron trihalide, and the solvent-complexed forms of these compounds. Alkyl borates for use in this invention have the general formula $B(OR)_3$, where R is an alkyl group. The alkyl groups preferably have from one to about six carbon atoms. Examples of suitable alkyl borates include trimethyl borate, triethyl borate, triisopropyl borate, tri(tert-butyl) borate, tri(cyclopentyl) borate, and tri (cyclohexyl) borate. Preferably, a boron trihalide is used, and the preferred boron trihalide for this embodiment is boron trifluoride and its solvent complexes, such as, for example, boron trifluoride diethyl etherate complex. Mixtures of boron trihalide and alkyl borate can also be used, but this is not preferred.

When a boron trihalide is used, it is preferably dissolved in a solvent. Preferred solvents are ethers; the highly preferred solvent is diethyl ether. Because the boron trihalide solution will be mixed with the fluoroaryl Grignard reagent, the solvent is necessarily anhydrous, although traces of moisture can be tolerated. If the solvent is too wet or the reactor contains moisture, the amount of fluoroaryl Grignard reagent needs to be increased to maintain the ratio of fluoroaryl Grignard reagent to boron trihalide.

At least a portion of the unreacted fluoroaromatic compound may be recovered and recycled to step(s) a) and/or b) after either the tris(fluoroaryl)borane or the tetrakis(fluoroaryl)borate anion is produced. In some embodiments, other fluoroaromatic compounds than the unreacted fluoroaromatic compound from step b) are present, and are also recovered after production of the tris(fluoroaryl)borane or the tetrakis(fluoroaryl)borate anion. Methods for removal and recovery of components include distillation, stripping at reduced pressure, or the like.

To produce tris(fluoroaryl)boranes, the ratio of fluoroaryl Grignard reagent to boron trihalide, boron trihalide solvent complex, or alkyl borate normally is in the range of from at least about 2.7:1 to about 3.3:1. Ratios greater than about 3.3:1 yield larger amounts of the corresponding tetrasubstituted borate anion, while ratios less than about 2.7:1 yield larger amounts of disubstituted borane, both of which are undesired side products in this embodiment of the invention. Preferred ratios are in the range of from about 2.9:1 to about 3.15:1, where anion formation is minimized. Most preferred are ratios in a range from about 3.0:1 to about 3.09:1.

During initial mixing of the boron trihalide solution or alkyl borate and the reaction product mixture produced in b), when proportions of fluoroaryl Grignard reagent and boron trihalide or alkyl borate are such that a tris(fluoroaryl)borane will be produced, the temperature may range from about −20° C. to about 5° C. It is more preferred to keep the initial mixing temperature between about −15° C. and about 3° C. Highly preferable is a range from about −10° C. to about 0° C. The time for initial mixing may range from about 5 minutes to two hours. More preferable is a mixing time ranging from about 10 minutes to about one hour; most preferred is a time between about 15 minutes and about 45 minutes. The temperature in step c) after initial mixing may range from about −15° C. to about 40° C.; amore preferable range is from about −10° C. to about 35° C. A range from about 0° C. to about 25° C. is most preferred. While the contact time for the various components in step c) can be anywhere from three to forty hours, a more useful range is from about five to about thirty hours. The contact time is preferably from about ten to about twenty hours.

In order to produce tetrakis(fluoroaryl)borate anions, the ratio of fluoroaryl Grignard reagent to boron trihalide, boron trihalide-solvent complex, or alkyl borate generally is in the range of from at least about 3.8:1 to about 7.0:1. Ratios less than about 3.8:1 yield larger amounts of the corresponding trisubstituted borane, an undesired side product in this embodiment. Preferred ratios are in the range from about 4.0:1 to about 5.0:1, where borane formation is minimized. Most preferred are ratios from about 4.2:1 to about 4.5: 1.

The temperature during initial mixing of the boron trihalide solution or alkyl borate and the reaction product mixture produced in b), when proportions of fluoroaryl Grignard reagent and boron trihalide or alkyl borate are such that a tetrakis(fluoroaryl)borate anion will be produced, may range from about 0° C. to about 50° C.; highly preferable is a range from about 15° C. to about 35° C. The time for initial mixing may range from about 5 minutes to two hours. More preferable is a mixing time ranging from about 10 minutes to about one hour; most preferred is a time between about 15 minutes and about thirty minutes. The temperature after initial mixing in step c) typically ranges from about 20° C. to about 80° C.; a more preferable range is from about 35° C. to about 70° C. A range from about 48° C. to about 65° C. is most preferred, especially when operating at pressures in the range of about 0 to about 20 psig (about 100 to about 240 kPa). While the contact time for the various components in step c) can be anywhere from one to twenty-four hours, a more useful range is from about three to about twenty hours. The contact time is preferably from about ten to about sixteen hours.

For a highly preferred practice of this invention when producing tris(fluoroaryl)boranes, the hydrocarbyl Grignard reagent is isopropylmagnesium bromide; the fluoroaromatic compound in step a) has a chlorine atom as its Grignard-reactive substituent; the fluoroaromatic compound in step b) has a bromine atom as its Grignard-reactive substituent; and (iii) is a liquid ethereal reaction medium. The reaction product mixture produced in b) is composed predominately of fluoroarylmagnesium bromide, isopropyl chloride, isopropyl bromide, fluoroaromatic compound which has a bromine atom as its Grignard-reactive substituent, and liquid ethereal reaction medium. The fluoroaromatic compound which has a bromine atom as its Grignard-reactive substituent present in the reaction product mixture produced in b) is consumed in situ by back-titration with isopropylmagnesium bromide prior to step c), forming more fluoroarylmagnesium bromide. A boron trihalide is used, and is boron trifluoride or a boron trifluoride etherate, and the proportions in step c) are such that the molar ratio of fluoroaryl Grignard reagent to boron trifluoride is in the range of about 2.7:1 to about 3.30:1.

A highly preferred practice of the invention when it is desired to produce tetra-kis(fluoroaryl)borate anions is as follows: the hydrocarbyl Grignard reagent is isopropylmagnesium bromide; the fluoroaromatic compound in step a) has a chlorine atom as its Grignard-reactive substituent; the fluoroaromatic compound in b) has a bromine atom as its Grignard-reactive substituent and (iii) is a liquid ethereal reaction medium. The reaction product mixture produced in b) is composed predominately of fluoroarylmagnesium bromide, isopropyl chloride, isopropyl bromide, fluoroaromatic compound which has a bromine atom as its Grignard-reactive substituent, and liquid ethereal reaction medium. The fluoroaromatic compound which has a bromine atom as its Grignard-reactive substituent present in the reaction product mixture produced in b) is consumed in situ by back-titration with isopropylmagnesium bromide prior to step c) in order to form more fluoroarylmagnesium bromide. In step c), a boron trihalide is used, and is boron trifluoride or a boron trifluoride-solvent complex, and the proportions are such that the molar ratio of fluoroaryl Grignard reagent to boron trifluoride is in the range of about 3.8:1 to about 7:1.

The following examples are presented for purposes of illustration, and are not intended to impose limitations on the scope of this invention.

EXAMPLE 1

To a diethyl ether solution of isopropyl magnesium bromide, chloropentafluorobenzene was added at 0 to 40° C.

under nitrogen with stirring in a period of thirty minutes, such that the isopropyl magnesium bromide was in 1.03 to 1.05 molar excess of the chloropentafluorobenzene. The mixture was stirred at 47 to 53° C.; after 5 to 10 hours, bromopentafluorobenzene was added to react with the excess isopropyl magnesium bromide, and the mixture was stirred at 25° C. for 1 hour. Any excess bromopentafluorobenzene was back-titrated in situ with isopropyl magnesium bromide to form more $C_6F_5MgBr$. The yield of $C_6F_5MgBr$ was 96.1%, and 3.9% $C_6F_5Cl$ remained, as determined by $^{19}F$ NMR, using $C_6H_5CF_3$ as a reference; no trace of iPrMgBr was seen with $^1H$ NMR.

EXAMPLE 2

Isopropyl magnesium bromide (30.0 g, 64.4 mmol) and 22.0 g dry diethyl ether were charged to a reaction vessel. Chloropentafluorobenzene (10.87 g, 53.7 mmol) was added at 38 to 39.7° C. under nitrogen with stirring in a period of one hour. The temperature of the mixture was raised to 47° C. during one hour with concurrent evaporation of about 20 g of diethyl ether, and the mixture was stirred at 44 to 47° C. for 11 hours. The mixture was then cooled to 20° C. The yield of $C_6F_5MgBr$ was 97.3%, with 2.5 to 2.7% $C_6F_5Cl$ and 8% iPrMgBr remaining, as determined by NMR, using $C_6H_5CF_3$ as a reference. To convert the 8% iPrMgBr to $C_6F_5MgBr$ and iPrBr, bromopentafluorobenzene was added, and the reaction mixture was stirred at 20° C. for thirty minutes.

EXAMPLE 3

Isopropyl magnesium bromide (10.0 g, 22.8 mmol) and 8.0 g dry diethyl ether were charged to a reaction vessel under nitrogen; the solution was cooled to 5 to 10° C. A mixture of chloropentafluorobenzene (2.03 g, 10 mmol) and pentafluorobenzene (1.68 g, 10 mmol) was added to the vessel at 10 to 38° C. under nitrogen with stirring during a three hour period. The reaction mixture was stirred at 46° C. and 14 psig (about 198 kPa) for three hours, followed by stirring at 55 to 60° C. and 20 psig (about 240 kPa) for eight hours. The mixture was cooled to 22° C., and NMR spectra were recorded, showing 99.7% conversion of chloropentafluorobenzene and 68% conversion of pentafluorobenzene. The reaction mixture was then stirred at 55 to 57° C. After 11 hours, 100% conversion of chloropentafluorobenzene and 81% conversion of pentafluorobenzene was seen by NMR. An additional 3.0 millimoles of pentafluorobenzene were added to the reaction mixture, which was then heated at 60 to 63° C. and 18 to 20 psig (about 225 to about 240 kPa) for 12 hours. NMR data now showed 100% conversion of chloropentafluorobenzene, 100% conversion of isopropylmagnesium bromide, and 3.34 millimoles of unreacted pentafluorobenzene. The yield of $C_6F_5MgBr$ was 88%, based on total chloropentafluorobenzene and pentafluorobenzene, as determined by NMR, with $C_6H_5CF_3$ as a reference.

EXAMPLE 4

Neat $BF_3.OEt_2$ was added to a solution of $C_6F_5MgBr$ in diethyl ether at 22 to 35° C. under nitrogen with stirring in a fifteen minute period, such that the molar ratio of $C_6F_5MgBr$ to $BF_3$ was 4.3:1. The mixture was stirred at 50 to 57° C. under pressure for 10 hours. The yield of $BrMgB(C_6F_5)_4$ was 93%, as determined by $^{19}F$ NMR, using $C_6H_5CF_3$ as a reference, based on the amount of $BF_3.OEt_2$ added.

EXAMPLE 5

Neat $BF_3.OEt_2$ was added to a solution of $C_6F_5MgBr$ in diethyl ether at −10 to −2° C. under nitrogen with stirring in a thirty minute period, such that the molar ratio of $C_6F_5MgBr$ to $BF_3$ was 3.09:1. The mixture was stirred at −9 to 24° C. for 16 to 18 hours. The yield of $B(C_6F_5)_3.OEt_2$ was 85.3%, and there were 1.88% $BrMgB(C_6F_5)_4$, 1.62% $C_6F_5H$, plus unknowns, present as impurities, as determined by $^{19}F$ NMR, using $C_6H_5CF_3$ as a reference, based on the amount of $BF_3.OEt_2$ added.

EXAMPLE 6

$C_6F_5MgBr$ in diethyl ether was cooled under nitrogen to 1° C. Neat $BF_3.OEt_2$ was added dropwise to the $C_6F_5MgBr$ solution at 1 to 4° C. under nitrogen with stirring in a forty minute period, such that the molar ratio of $C_6F_5MgBr$ to $BF_3.OEt_2$ was 3.065:1. The mixture was stirred and heated to 10° C. for 1 hour, to 18° C. for another hour, and then at 18 to 21° C. for nine hours. The yield of $B(C_6F_5)_3.OEt_2$ was 84.8%, based on $BF_3.OEt_2$; the yield was 82.9%, based on $C_6F_5MgBr$, both as determined by NMR with $C_6H_5CH_3$ as reference.

EXAMPLE 7

The procedure of Example 6 was followed, except that the molar ratio of $C_6F_5MgBr$ to $BF_3.OEt_2$ was 3.05:1. The yield of $B(C_6F_5)_3.OEt_2$ was 82%, based on $C_6F_5MgBr$.

EXAMPLE 8

Neat $BF_3.OEt_2$ was added to a solution of $C_6F_5MgBr$ in diethyl ether in a 100-gallon reactor at 22 to 35° C. under nitrogen with stirring, such that the molar ratio of $C_6F_5MgBr$ to $BF_3$ is 4.3:1. The mixture was stirred at 60 to 63° C. under pressure for 16–20 hours.

The yield of $BrMgB(C_6F_5)_4$ was 87%, as determined by $^{19}F$ NMR, using $C_6H_5CF_3$ as a reference, based on the amount of $BF_3.OEt_2$ added.

When carrying out this invention, Examples 1–3 described above can be followed by replacing chloropentafluorobenzene, bromopentafluorobenzene, and pentafluorobenzene with a fluoroaromatic compound in which bonded directly to an aromatic ring are (I) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom. Similarly, $C_6F_5MgBr$ can be replaced with a fluoroaryl Grignard reagent formed by practicing this invention, and Examples 4–8 described above can be followed to carry out this invention.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises:
    a) forming a mixture comprising (i) hydrocarbyl Grignard reagent, (ii) at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, and (iii) an anhydrous liquid organic reaction medium, in which the molar ratio of (i) to (ii) is greater than 1, such that a reaction product mixture is formed comprising fluoroaryl Grignard reagent and excess hydrocarbyl Grignard reagent; and
    b) mixing with at least a portion of said reaction product mixture produced in a) an amount of at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, at least sufficient to react with said excess hydrocarbyl Grignard reagent to thereby produce a further reaction product mixture composed predominately of fluoroaryl Grignard reagent and anhydrous liquid organic reaction medium.

2. A process as in claim 1 wherein in a) and in b), (1) is at least two perfluorohydrocarbyl groups.

3. A process as in claim 2 wherein said perfluorohydrocarbyl groups are trifluoromethyl groups.

4. A process as in claim 1 wherein in a), (2) is one halogen atom other than a fluorine atom and at least one hydrogen atom, and wherein said halogen atom is a chlorine atom.

5. A process as in claim 1 wherein in b), (2) is one halogen atom other than a fluorine atom and at least one hydrogen atom, and wherein said halogen atom is a bromine atom.

6. A process as in claim 1 wherein in a) and in b), (1) is at least two perfluorollydrocarbyl groups; wherein in a) and in b), (2) is one halogen atom other than a fluorine atom and at least one hydrogen atom; wherein in a) said halogen atom is a chlorine atom; and wherein in b) said halogen atom is a bromine atom.

7. A process as in claim 6 wherein said perfluorohydrocarbyl groups are trifluoromethyl groups.

8. A process as in claim 1 wherein (iii) in a) is at least predominately a liquid ethereal reaction medium.

9. A process as in claim 1 wherein in b) said amount of said at least one fluoroaromatic compound is in excess relative to said excess hydrocarbyl Grignard reagent such that said reaction product mixture comprises an excess of said fluoroaromatic compound.

10. A process as in claim 9 wherein said excess fluoroaromatic compound in the reaction product mixture in b) is back-titrated with hydrocarbyl Grignard reagent.

11. A process as in claim 1 wherein the temperature of the mixture in a) and/or b) is in the range of from about 0° C. to about 60° C.

12. A process as in claim 1 wherein the pressure in a) and/or b) is in the range of from about 0 psig to about 20 psig.

13. A process as in claim 1 wherein in a) and in b), (1) is at least two perfluorohydrocarbyl groups; wherein in a) and in b), (2) is one halogen atom other than a fluorine atom and at least one hydrogen atom; wherein in a) said halogen atom is a chlorine atom; wherein in b) said halogen atom is a bromine atom; and wherein in b) said amount of said at least one fluoroaromatic compound is in excess relative to said excess hydrocarbyl Grignard reagent such that said reaction product mixture comprises an excess of said fluoroaromatic compound.

14. A process as in claim 13 wherein said excess fluoroaromatic compound in the reaction product mixture in b) is back-titrated with hydrocarbyl Grignard reagent.

15. A process which comprises
    a) contacting a mixture comprising a fluoroaryl Grignard reagent, a hydrocarbyl Grignard reagent, and a liquid organic medium, with at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, in an amount at least equivalent to the amount of said hydrocarbyl Grignard reagent, and
    b) maintaining the resultant mixture at a temperature at least high enough to cause hydrocarbyl Grignard reagent to be converted into fluoroaryl Grignard reagent.

16. A process according to claim 15 wherein at least the mixture of a) comprises at least predominately a liquid ethereal reaction medium.

17. A process as in claim 15 wherein in a), (1) is at least two perfluorohydrocarbyl groups.

18. A process as in claim 17 wherein said perfluorohydrocarbyl groups are trifluoromethyl groups.

19. A process according to claim 15 wherein in a), (2) is one halogen atom other than a fluorine atom and at least one hydrogen atom, and wherein said halogen atom is a bromine atom.

20. A process which comprises:
    a) forming a mixture comprising (i) hydrocarbyl Grignard reagent, (ii) at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, and (iii) an anhydrous liquid organic reaction medium, in which the molar ratio of (i) to (ii) is greater than 1, such that a reaction product mixture is formed comprising fluoroaryl Grignard reagent and excess hydrocarbyl Grignard reagent;

b) mixing with at least a portion of said reaction product mixture produced in a) an amount of at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, said amount being in excess relative to said hydrocarbyl Grignard reagent such that there is produced a further reaction product mixture composed predominately of fluoroaryl Grignard reagent, anhydrous liquid organic reaction medium, and unreacted fluoroaromatic compound; and c) mixing a boron trihalide, a boron trihalide-solvent complex, or an alkyl borate with at least a portion of said reaction product mixture produced in b) in proportions such that a tris(fluoroaryl)borane is produced.

21. A process as in claim 20 in which the temperature during initial mixing of the boron trihalide or alkyl borate and the reaction product mixture produced in b) containing the fluoroaryl Grignard reagent is in the range of from about −20° C. to about 5° C.

22. A process as in claim 21 in which the temperature in c) after initial mixing is in the range of from about −15° C. to about 40° C.

23. A process as in claim 20 in which at least a portion of said unreacted fluoroaromatic compound is recovered from c) and recycled to a) and/or b) after the tris(fluoroaryl) borane is produced.

24. A process as in claim 20 wherein in a) and in b), (2) is one halogen atom other than a fluorine atom and at least one hydrogen atom, and wherein in a) said halogen atom is a chlorine atom; wherein in b) said halogen atom is a bromine atom; wherein (iii) is a liquid ethereal reaction medium; wherein the reaction product mixture produced in b) is composed predominately of fluoroarylmagnesium bromide, isopropyl chloride, isopropyl bromide, fluoroaromatic compound in which said halogen atom is a bromine atom, and said liquid ethereal reaction medium; and wherein the fluoroaromatic compound in which said halogen atom is a bromine atom in the reaction product mixture produced in b) is consumed by back-titration with hydrocarbyl Grignard reagent prior to step c).

25. A process which comprises:

a) forming a mixture comprising (i) hydrocarbyl Grignard reagent, (ii) at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a halogen atom other than a fluorine atom and at least one hydrogen atom, and (iii) an anhydrous liquid organic reaction medium, in which the molar ratio of (i) to (ii) is greater than 1, such that a reaction product mixture is formed comprising fluoroaryl Grignard reagent and excess hydrocarbyl Grignard reagent;

b) mixing with at least a portion of said reaction product mixture produced in a) an amount of at least one fluoroaromatic compound in which bonded directly to an aromatic ring are (1) at least two fluorine atoms, or at least two perfluorohydrocarbyl groups, or at least one fluorine atom and at least one perfluorohydrocarbyl group, and (2) at least two hydrogen atoms, or a combination of one halogen atom other than a fluorine atom and at least one hydrogen atom, said amount being in excess relative to said hydrocarbyl Grignard reagent such that there is produced a further reaction product mixture composed predominately of fluoroaryl Grignard reagent, anhydrous liquid organic reaction medium, and unreacted fluoroaromatic compound; and c) mixing a boron trihalide, a boron trihalide-solvent complex, or an alkyl borate with at least a portion of said reaction product mixture produced in b) in proportions such that a salt of a tetrakis(fluoroaryl)borate anion is produced.

26. A process as in claim 25 in which the temperature during initial mixing of the boron trihalide or alkyl borate and the reaction product mixture produced in b) containing the fluoroaryl Grignard reagent is in the range of from about 0° C. to about 50° C.

27. A process as in claim 26 in which the temperature in step c) after initial mixing is in the range of from about 20° C. to about 80° C.

28. A process according to claim 25 wherein the pressure is in the range of from about 0 psig to about 20 psig.

29. A process as in claim 25 in which at least a portion of said unreacted fluoroaromatic compound is recovered from c) and recycled to a) and/or b) after the tetrakis(fluoroaryl) borate anion is produced.

30. A process as in claim 25 wherein in a) and in b), (2) is one halogen atom other than a fluorine atom and at least one hydrogen atom, and wherein in a) said halogen atom is a chlorine atom; wherein in b) said halogen atom is a bromine atom; wherein (iii) is a liquid ethereal reaction medium; wherein the reaction product mixture produced in b) is composed predominately of fluoroarylmagnesium bromide, isopropyl chloride, isopropyl bromide, fluoroaromatic compound in which said halogen atom is a bromine atom, and said liquid ethereal reaction medium; and wherein the fluoroaromatic compound in which said halogen atom is a bromine atom in the reaction product mixture produced in b) is consumed by back-titration with hydrocarbyl Grignard reagent prior to step c).

* * * * *